United States Patent
Avellanet

[19]

[11] Patent Number: 6,137,060
[45] Date of Patent: Oct. 24, 2000

[54] MULTIFILAMENT DRAWN RADIOPAQUE HIGHLY ELASTIC CABLES AND METHODS OF MAKING THE SAME

[75] Inventor: Francisco J. Avellanet, Coral Gables, Fla.

[73] Assignee: General Science and Technology Corp, Miami, Fla.

[21] Appl. No.: 09/060,969

[22] Filed: Apr. 15, 1998

Related U.S. Application Data

[63] Continuation-in-part of application No. 08/843,405, May 2, 1997, Pat. No. 5,994,647, and a continuation-in-part of application No. 08/963,686, Nov. 4, 1997, Pat. No. 6,049,042, and a continuation-in-part of application No. 08/856,571, May 15, 1997, Pat. No. 6,019,736, and a continuation-in-part of application No. PCT/US97/18057, Oct. 7, 1997.

[51] Int. Cl.⁷ ...................................................... H01B 5/10
[52] U.S. Cl. .......................................................... 174/128.1
[58] Field of Search .............................. 174/128.1, 128.2, 174/125.1, 126.1

[56] References Cited

U.S. PATENT DOCUMENTS

| | | | |
|---|---|---|---|
| H1239 | 10/1993 | Dusek ........................................ | 264/63 |
| 251,114 | 12/1881 | Hallidie . | |
| 1,742,172 | 12/1929 | Atwood . | |
| 1,888,076 | 11/1932 | Evans . | |
| 1,888,807 | 11/1932 | Rivers . | |
| 1,904,162 | 4/1933 | Milliken . | |
| 1,943,082 | 1/1934 | MacKenzie .............................. | 261/49 |
| 1,943,086 | 1/1934 | McKnight ................................ | 173/264 |
| 1,943,087 | 1/1934 | Potter ...................................... | 173/264 |
| 2,071,709 | 2/1937 | Riddle ...................................... | 117/16 |
| 2,135,800 | 11/1938 | Davignon .................................... | 88/52 |
| 2,154,551 | 4/1939 | Wodtke ................................... | 174/128 |
| 2,156,652 | 5/1939 | Harris ........................................ | 57/145 |
| 2,396,734 | 3/1946 | Williams, Jr. ........................... | 174/128 |
| 2,427,507 | 9/1947 | Powell, 3rd. ............................. | 57/164 |
| 2,978,860 | 4/1961 | Campbell .................................... | 57/148 |
| 3,006,384 | 10/1961 | Brown et al. ............................. | 139/425 |
| 3,083,817 | 4/1963 | Campbell .................................... | 205/2 |
| 3,130,536 | 4/1964 | Peterson et al. .......................... | 57/161 |
| 3,131,469 | 5/1964 | Glaze ................................. | 174/128.1 X |
| 3,195,299 | 7/1965 | Dietz ........................................ | 57/149 |
| 3,234,722 | 2/1966 | Gilmore .................................... | 57/145 |
| 3,261,908 | 7/1966 | Roche et al. ............................. | 174/128.1 |
| 3,295,310 | 1/1967 | Beighley .................................... | 57/145 |
| 3,333,045 | 7/1967 | Fisher et al. ............................... | 174/20 |
| 3,352,098 | 11/1967 | Gilmore .................................... | 57/147 |
| 3,383,704 | 5/1968 | Schoerner et al. ........................ | 57/145 |
| 3,395,528 | 8/1968 | Lucht et al. ............................... | 57/145 |
| 3,444,684 | 5/1969 | Schoerner et al. ........................ | 57/161 |
| 3,601,970 | 8/1971 | Roberts et al. ........................... | 57/153 |
| 3,699,768 | 10/1972 | Roberts et al. ........................... | 57/144 |

(List continued on next page.)

FOREIGN PATENT DOCUMENTS

| | | | |
|---|---|---|---|
| 197692 | 5/1923 | United Kingdom ............ | 174/128.1 X |

OTHER PUBLICATIONS

Hesterlee, Jerry M., "Trapwire Constructions," Wire Technology International, pp. 51–53, Mar. 1997.

*Primary Examiner*—Dean A. Reichard
*Attorney, Agent, or Firm*—David P. Gordon; David S. Jacobson; Thomas A. Gallagher

[57] ABSTRACT

A highly flexible radiopaque cable includes two, and preferably three or more strands of nickel-titanium (NiTi) alloy wire which are twined about a higher density core wire preferably made of at least one of silver, gold or platinum-iridium to form a wire rope. The wire rope is drawn through successive dies to reduce its diameter until the outer surface of the cable is substantially smooth, the cross section of the cable is substantially circular, and the overall diameter of the wire rope is reduced by 20–50%. The cable is then annealed to remove the effects of cold working. The resulting cable has been found to have a substantially equal or improved flexibility (i.e., a lower modulus of elasticity) relative to single strand nickel-titanium wires of the same diameter and a higher radiopacity. In an alternative embodiment, no core wire is utilized, and the higher density wire is drawn with two or more strands of NiTi wire. In another embodiment, the higher density wire is radioactive.

23 Claims, 2 Drawing Sheets

U.S. PATENT DOCUMENTS

| | | | |
|---|---|---|---|
| 3,812,666 | 5/1974 | Sarracino | 57/58.52 |
| 3,822,542 | 7/1974 | Naud et al. | 57/145 |
| 3,831,370 | 8/1974 | Gilmore | 57/145 |
| 3,842,185 | 10/1974 | Raw et al. | 174/23 R |
| 3,883,278 | 5/1975 | Hass | 425/135 |
| 3,883,371 | 5/1975 | Geary | 148/32 |
| 3,900,347 | 8/1975 | Lorenzetti et al. | 148/12 B |
| 3,922,841 | 12/1975 | Katsumata et al. | 57/145 |
| 3,923,003 | 12/1975 | Carden | 118/405 |
| 3,934,446 | 1/1976 | Avitzur | 72/206 |
| 3,942,309 | 3/1976 | Cahill | 57/9 |
| 3,955,390 | 5/1976 | Geary | 72/64 |
| 3,961,514 | 6/1976 | Geary | 72/274 |
| 3,972,304 | 8/1976 | Boucher | 118/44 |
| 3,990,874 | 11/1976 | Schulman | 65/4 B |
| 4,020,829 | 5/1977 | Willson | 128/2 M |
| 4,079,510 | 3/1978 | McGrath et al. | 29/624 |
| 4,125,741 | 11/1978 | Wahl et al. | 174/120 |
| 4,133,167 | 1/1979 | Schofield | 57/12 |
| 4,173,235 | 11/1979 | Tipper | 140/82 |
| 4,201,250 | 5/1980 | Walling et al. | 141/250 |
| 4,212,151 | 7/1980 | Schauffele et al. | 57/9 |
| 4,215,703 | 8/1980 | Willson | 128/772 |
| 4,311,001 | 1/1982 | Glushko et al. | 57/215 |
| 4,328,662 | 5/1982 | Bretegnier et al. | 57/58.61 |
| 4,330,956 | 5/1982 | McCarthy | 43/4 |
| 4,349,694 | 9/1982 | Vives | 174/128 R |
| 4,352,697 | 10/1982 | Adams et al. | 148/2 |
| 4,354,880 | 10/1982 | Adams et al. | 148/2 |
| 4,406,058 | 9/1983 | Dixon | 29/809 |
| 4,456,491 | 6/1984 | Adams et al. | 148/2 |
| 4,471,527 | 9/1984 | Nishijima | 29/872 |
| 4,473,995 | 10/1984 | Gentry | 57/9 |
| 4,514,058 | 4/1985 | Walton | 350/96.23 |
| 4,525,598 | 6/1985 | Tsukamoto et al. | 174/128 |
| 4,529,837 | 7/1985 | Borden | 174/128 |
| 4,534,363 | 8/1985 | Gold | 128/772 |
| 4,548,206 | 10/1985 | Osborne | 128/772 |
| 4,579,127 | 4/1986 | Haacke | 128/772 |
| 4,634,042 | 1/1987 | Smith | 228/173.4 |
| 4,651,513 | 3/1987 | Dambre | 57/217 |
| 4,654,477 | 3/1987 | Isoda | 174/128 R |
| 4,679,387 | 7/1987 | Weidenhaupt et al. | 57/212 |
| 4,682,607 | 7/1987 | Vaillancourt | 128/772 |
| 4,689,444 | 8/1987 | Burgess | 174/128 R |
| 4,705,096 | 11/1987 | Chia | 164/476 |
| 4,731,134 | 3/1988 | Alloin et al. | 156/53 |
| 4,759,806 | 7/1988 | Dambre | 148/12 B |
| 4,763,466 | 8/1988 | Abe et al. | 57/213 |
| 4,777,324 | 10/1988 | Lee | 174/34 |
| 4,778,246 | 10/1988 | Carroll | 350/96.23 |
| 4,843,696 | 7/1989 | Gentry et al. | 29/33 F |
| 4,922,924 | 5/1990 | Gambale | 128/772 |
| 4,925,445 | 5/1990 | Sakamoto et al. | 604/95 |
| 5,018,993 | 5/1991 | Durham | 439/801 |
| 5,069,217 | 12/1991 | Flesichhacker | 128/657 |
| 5,074,140 | 12/1991 | Sanders | 72/248 |
| 5,118,906 | 6/1992 | Kudoh et al. | 174/128.1 X |
| 5,129,890 | 7/1992 | Bates et al. | 604/281 |
| 5,133,121 | 7/1992 | Birbeck et al. | 29/872 |
| 5,147,662 | 9/1992 | Nishijima et al. | 425/500 |
| 5,167,399 | 12/1992 | Delomel | 254/134.3 R |
| 5,190,546 | 3/1993 | Jervis | 606/78 |
| 5,211,772 | 5/1993 | Ashida et al. | 148/336 |
| 5,213,111 | 5/1993 | Cook et al. | 128/772 |
| 5,215,246 | 6/1993 | Thompson et al. | 228/171 |
| 5,217,026 | 6/1993 | Stoy et al. | 128/772 |
| 5,230,348 | 7/1993 | Ishibe et al. | 128/772 |
| 5,240,520 | 8/1993 | Tarui et al. | 148/532 |
| 5,242,759 | 9/1993 | Hall | 428/610 |
| 5,251,640 | 10/1993 | Osborne | 128/772 |
| 5,260,516 | 11/1993 | Blackmore | 174/113 A |
| 5,286,577 | 2/1994 | Premkumar et al. | 428/558 |
| 5,322,508 | 6/1994 | Viera | 604/52 |
| 5,333,620 | 8/1994 | Moutafis et al. | 128/772 |
| 5,334,166 | 8/1994 | Palestrant | 604/265 |
| 5,343,934 | 9/1994 | Wilson | 164/476 |
| 5,368,661 | 11/1994 | Nakamura et al. | 148/512 |
| 5,417,690 | 5/1995 | Sennett | 606/61 |
| 5,418,333 | 5/1995 | Sanders | 174/129 |
| 5,429,139 | 7/1995 | Sauter | 128/772 |
| 5,433,200 | 7/1995 | Flesichhacker | 128/657 |
| 5,437,288 | 8/1995 | Schwartz et al. | 128/772 |
| 5,437,748 | 8/1995 | Bhagwat et al. | 148/532 |
| 5,439,000 | 8/1995 | Gunderson | 128/664 |
| 5,451,718 | 9/1995 | Dixon | 174/102 R |
| 5,483,022 | 1/1996 | Mar | 174/128.1 X |
| 5,486,183 | 1/1996 | Middleman et al. | 606/127 |
| 5,520,194 | 5/1996 | Miyata et al. | 128/772 |
| 5,535,612 | 7/1996 | Vijayakar | 72/43 |
| 5,571,086 | 11/1996 | Kaplan et al. | 604/96 |
| 5,571,087 | 11/1996 | Ressemann | 604/96 |
| 5,571,094 | 11/1996 | Sirhan | 604/284 |
| 5,588,443 | 12/1996 | Davidson | 128/772 |
| 5,597,378 | 1/1997 | Jervis | 606/78 |
| 5,616,197 | 4/1997 | Helfer et al. | 152/527 |
| 5,632,746 | 5/1997 | Middleman et al. | 606/78 |
| 5,709,760 | 1/1998 | Prakash | 152/556 |
| 5,718,159 | 2/1998 | Thompson | 87/33 |

MULTIFILAMENT DRAWN RADIOPAQUE HIGHLY ELASTIC CABLES AND METHODS OF MAKING THE SAME

This application is a continuation-in-part of U.S. Ser. No. 08/843,405 filed May 2, 1997 now U.S. Pat. No. 5,994,647, and a continuation-in-part of U.S. Ser. No. 08/963,686 filed Nov. 4, 1997 now U.S. Pat. No. 6,049,042, and a continuation-in-part of U.S. Ser. No. 08/856,571 filed May 15, 1997 now U.S. Pat. No. 6,019,736, and a continuation-in-part of PCT/US97/18057 filed Oct. 7, 1997 and claiming priority from U.S. Ser. No. 08/730,489 filed Oct. 11,1996 (now abandoned) and Ser. No. 08/856,571 filed May 15, 1997 all of which are hereby incorporated by reference herein in their entireties.

BACKGROUND OF THE INVENTION

1. Field of the Invention

The present invention relates to wires having a low modulus of elasticity. More particularly, the present invention is related to improvements in radiopaque wires; i.e., wires which may be seen under fluoroscopy (X-ray), and methods of making the radiopaque wires. The present invention has particular application to the medical guidewire arts of some of the parent applications hereof, and to the medical stent arts, although it is not limited to the medical arts.

2. State of the Art

Wire is manufactured from ingots using a rolling mill and a drawing bench. The preliminary treatment of the material to be manufactured into wire is done in the rolling mill where white hot billets (square section ingots) are rolled to round wire rod. The action of atmospheric oxygen causes a coating of mill scale to form on the hot surface of the rod and must be removed. This descaling can be done by various mechanical methods (e.g., shot-blasting) or by pickling, i.e., immersion of the wire rod in a bath of dilute sulfuric or hydrochloric acid or mixtures with hydrofluoric acid. After pickling, the wire rod may additionally undergo a jolting treatment which dislodges the scale loosened by the acid. The remaining acid is removed by immersion of the wire rod in lime water.

The actual process of forming the wire is called drawing and is carried out on the metal in a cold state with a drawing bench. Prior art FIG. 1 shows a simple drawing bench 10. The wire 12 is pulled through a draw plate 14 which is provided with a number of holes, e.g. 16, (dies) of various diameters. These dies have holes which taper from the diameter of the wire 12 that enters the die to the smaller diameter of the wire 12' that emerges from the die. The thick wire rod 12 is coiled on a vertical spool 18 called a swift and is pulled through the die by a rotating drum 20 mounted on a vertical shaft 22 which is driven by bevel gearing 24. The drum can be disconnected from the drive by means of a clutch 26. To pass a wire through a die, the end of the wire is sharpened to a point and threaded through the die. It is seized by a gripping device and rapidly pulled through the die. This is assisted by lubrication of the wire. Each passage through a die reduces the diameter of the wire by a certain amount. By successively passing the wire through dies of smaller and smaller diameter, thinner and thinner wire is obtained. The dies used in the modern wire industry are precision-made tools, usually made of tungsten carbide for larger sizes or diamond for smaller sizes. The die design and fabrication is relatively complex and dies may be made of a variety of materials including single crystal natural or synthetic diamond, polycrystalline diamond or a mix of tungsten and cobalt powder mixed together and cold pressed into the carbide nib shape.

A cross section of die 16 is shown in prior art FIG. 2. Generally, the dies used for drawing wire have an outer steel casing 30 and an inner nib 32 which, as mentioned above, may be made of carbide or diamond or the like. The die has a large diameter entrance 34, known as the bell, which is shaped so that wire entering the die will draw lubricant with it. The shape of the bell causes the hydrostatic pressure to increase and promotes the flow of lubricant into the die. The region 36 of the die where the actual reduction in diameter occurs is called the approach angle. In the design of dies, the approach angle is an important parameter. The region 38 following the approach angle is called the bearing region. The bearing region does not cause diametric reduction, but does produce a frictional drag on the wire. The chief function of the bearing region 38 is to permit the conical approach surface 36 to be refinished (to remove surface damage due to die wear) without changing the die exit. The last region 40 of the die is called the back relief. The back relief allows the metal wire to expand slightly as the wire leaves the die. It also minimizes the possibility of abrasion taking place if the drawing stops or if the die is out of alignment with the path of the wire.

Although wire drawing appears to be a simple metalworking process, those skilled in the art will appreciate that many different parameters affect the physical quality of the drawn wire. Among these parameters, draw stress and flow stress play an important role. If these parameters are not carefully considered, the drawn wire may have reduced tensile strength. A discussion of the practical aspects of wire drawing can be found in Wright, Roger N., "Mechanical Analysis and Die Design", Wire Journal, October 1979, the complete disclosure of which is hereby incorporated by reference herein.

The wire forming processes described above may be used to form different kinds of wires. Generally, various characteristics of the formed wire are of interest, depending upon the art in which the wire is to be used. These aspects include, but are not limited to the electrical resistance, tensile strength, and flexibility of the wire. Wire flexibility is particularly important in the medical arts which utilize wires in inter alia stents and guidewires, although wire flexibility is important in other arts as well. For that reason, the medical arts have had much interest recently in nickel-titanium (Nitinol) alloy wires which exhibit superelastic characteristics.

While Nitinol guidewires and stents exhibit desirable wire flexibility for medical procedures, very fine (i.e., small diameter) Nitinol wires are not easily seen during a fluoroscopy procedure. In particular, in the case of guidewires where it is desirable to provide a very flexible distal portion (tip) to the guidewire, the tip of the Nitinol guidewire is typically ground down to a diameter on the order of 0.008" or smaller. With such a small diameter, the X-ray absorption is difficult to detect. Thus, the art has gone to great lengths and expense to provide flexible radiopaque coils around the distal end of the Nitinol guidewire (see, e.g., U.S. Pat. No. 5,520,194 to Miyata et al.). While metal coils formed from material such as platinum operate effectively in providing radiopacity while maintaining flexibility, the coils are difficult to manufacture and attach to the Nitinol guidewire owing, in part, to their dissimilarity with the guidewire material.

SUMMARY OF THE INVENTION

It is therefore an object of the invention to provide extremely flexible radiopaque wires.

It is another object of the invention to provide flexible small diameter radiopaque wires which are suitable for use as medical guidewires or as wires of a medical stent.

It is a further object of the invention to provide flexible wires which when ground to a very small diameter are sufficiently radiopaque to be seen in a fluoroscopy procedure.

In accord with this object which will be discussed in detail below, the radiopaque wire of the invention generally comprises two or more strands of nickel-titanium alloy wire and a strand of a high density wire such as gold, silver, or platinum-iridium, which are twisted to form a wire rope, drawn through successive dies to generate a radiopaque wire or cable of reduced diameter, and preferably annealed to remove the effects of cold working. For purposes herein, the final product is called either a "cable" or a "wire", because the final product may be substituted for a wire, although it is formed from twisted drawn strands which make it appear as a cable.

In the preferred embodiment of the invention, three or more nickel-titanium strands are wound around a single central high density strand of gold, silver or platinum-iridium wire, and the resulting rope is drawn through several dies until the diameter of the outer surface of the cable or wire is substantially smooth and has a diameter which is reduced by 20–50% over the diameter of the rope. In most cases, the resulting radiopaque cable or wire has been found to have a flexibility approximately equal to or better than single strand nickel-titanium wires of the same diameter.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
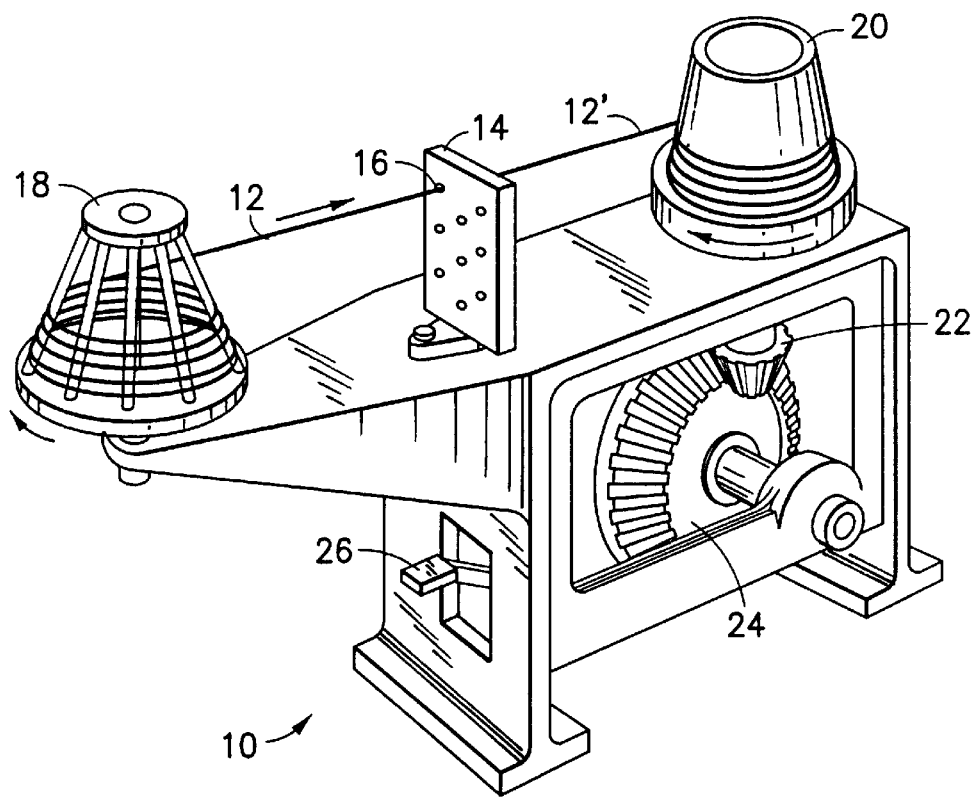
FIG. 1 is a schematic perspective view of a prior art wire drawing apparatus.
Figure 2:
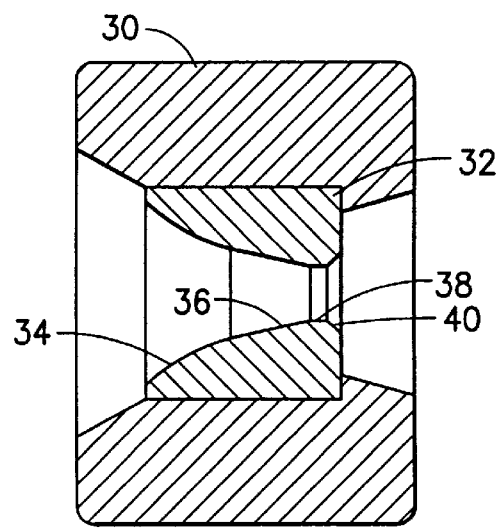
FIG. 2 is a schematic sectional view of a prior art drawing die.
Figure 3:
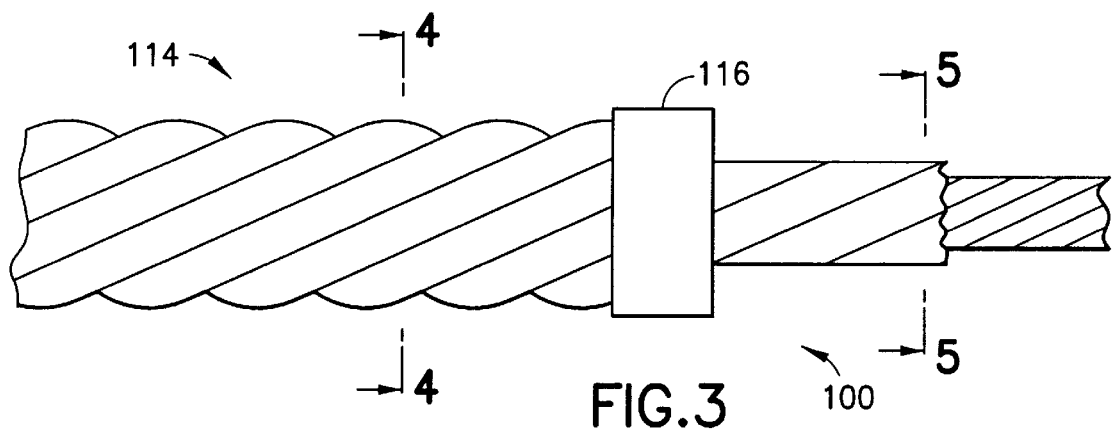
FIG. 3 is a schematic view of a wire rope being drawn through a die according to the invention.
Figure 4:
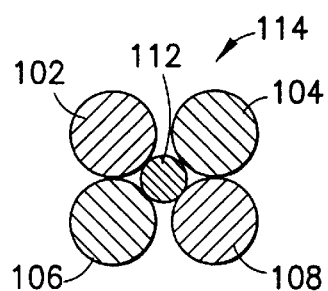
FIG. 4 is a cross sectional view taken along line 4—4 in FIG. 3.
Figure 5:
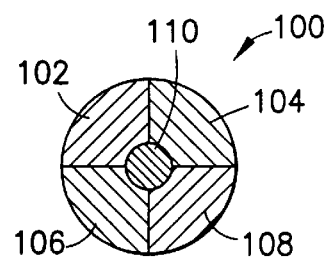
FIG. 5 is a cross sectional view taken along line 5—5 in FIG. 3.

Referring now to FIGS. 3 through 5, a highly flexible wire 100 according to the invention made from strands of nickel-titanium alloy wire and from a strand of high density wire such as gold, silver or platinum-iridium is manufactured according to the following method. Four strands of nickel-titanium alloy (e.g., Nitinol) wire 102, 104, 106, 108 are twined (twisted) together about a high density core wire 112 to form a wire rope 114. The wire rope 114 is pulled through a die 116 using known wire drawing methods and apparatus whereby its diameter is decreased. Preferably, the wire rope 114 is successively drawn through dies of decreasing diameter. During the drawing process, the wires 102, 104, 106, 108, 112 are plastically deformed. After the successive drawing is completed, the wire or cable 100 assumes a substantially circular cross section as shown in FIG. 5. The wire or cable 100 is then preferably subjected to annealing at, e.g., 500° C. for one minute, to remove the effects of cold-working, and the cable may then be cut to size. The drawing and annealing process is preferably conducted as a continuous process. The result of the process is a cable 100 which exhibits flexibility substantially equal to or greater than a single strand nickel-titanium alloy wire of the same cross section as will be discussed in more detail below. Moreover, the cable 100 exhibits a density (and hence radiopacity) which is greater than the density of a single strand nickel-titanium alloy wire, and further exhibits desirable and advantageous conductivity characteristics.

According to the presently preferred embodiment, the wire rope 114 of a plurality of NiTi wires and a higher density Au, Ag, or Pt—Ir core wire is successively pulled through multiple dies of decreasing diameter. The resulting cable 100 has a diameter which is approximately 20–50% smaller, and preferably at least 30% smaller than the diameter of the wire rope 114.

According to another embodiment of the invention, rather than using a gold, silver, or platinum-iridium core wire in conjunction with the NiTi wires, another relatively high density core wire which is radioactive is utilized. The radioactive wire may be formed from a metal alloy such as Pt—Ir utilizing a radioactive iridium, or from a radioactive alloy such as tungsten/rhenium, or a metal such as palladium having a radioactive element such as palladium-103 therein, or another relatively high density metal (such as gold) which is seeded with radioactive particles of any suitable type (e.g., yttrium-90). The resulting radioactive, radiopaque wire may be particularly useful in certain medical applications. See, "Reducing Restenosis with Endovascular Brachytherapy", *Medpro Month*, Vol. VIII, No. 1, pp. 25–32 (January 1998).

EXAMPLE 1

Illustrated by FIGS. 4 and 5 described above, four strands of 0.005 inch diameter Nitinol wire were helically twisted about a single strand of 0.003 inch diameter gold core wire at a lay length of approximately 0.050 inches to form a wire rope of approximately 0.013" diameter. The wire rope was fed through successive dies of approximately 0.012", 0.0105", 0.009", and 0.0075" diameters to form a Nitinol/gold cable. After each die, the cable rebounded to a slightly larger diameter than the diameter of the die. Thus, after the last die, the Nitinol/gold cable had a diameter of approximately 0.0085"±0.0005". The so-formed Nitinol/gold wire or cable was then annealed for approximately one minute at a temperature of approximately 500° C. to remove the effects of cold-working from the cable and return the superelastic properties. Pieces of the resulting twisted and drawn Nitinol/gold cable were then subjected to bend radius testing by wrapping pieces of the cables around pins of different diameters and by clamping the cable back on itself with a pair of pliers to simulate a zero-diameter bend. Comparison tests were conducted on 0.008" diameter Nitinol wires (single strand). The results of the bend radius testing are set forth in Table 1, with percent recovery calculated according to (180°−x°)/180°, where x° is the angle of set taken by the wire or cable from longitudinal axis of the wire after the bend:

TABLE 1

| Pin Diameter (inch) | % Recovery NiTi/Au cable | % Recovery NiTi Wire |
|---|---|---|
| .247 | 100 | 99.17 |
| .231 | 100 | 99.17 |
| .201 | 100 | 99.44 |
| .169 | 100 | 99.44 |
| .139 | 99.89 | 99.56 |
| .109 | 99.44 | 98.33 |
| .078 | 99.72 | 98.22 |
| 050 | 98.89 | 92.50 |
| .036 | 97.22 | 70.00 |
| .024 | 95.56 | 56.67 |
| 0 diameter bend | 74.4 | 47.22 |

From the results of the tests set forth in Table 1, it will be appreciated that the Nitinol/gold cable of the invention exhibited increased flexibility relative to the same diameter Nitinol wire. For example, the NiTi/Au cable exhibited 100% recovery at a bend diameter of approximately one-half the bend diameter that the Nitinol wire had less than full recovery. Also, at pin diameters of 0.036" and smaller, the NiTi/Au cable exhibited much better recovery than the same diameter NiTi wire. Thus, the recoverable elastic strain of the Nitinol/gold cable was higher than the recoverable elastic strain of the Nitinol wire. Furthermore, it is believed that the Nitinol/gold cable of the invention exhibited high elastic characteristics without the Nitinol entering the stress-induced martensite phase. In addition to the increased flexibility, the Nitinol/gold cable of the invention exhibited increased radiopacity relative to the same diameter Nitinol wire.

EXAMPLE 2

Illustrated by FIGS. 4 and 5 described above, four strands of 0.005 inch diameter Nitinol wire were helically twisted about a single strand of 0.003 inch diameter silver core wire at a lay length of approximately 0.050 inches to form a wire rope of approximately 0.013" diameter. The wire rope was fed through successive dies of approximately 0.012", 0.0105", 0.009", and 0.0075" diameters to form a Nitinol/silver cable. After each die, the cable rebounded to a slightly larger diameter than the diameter of the die. Thus, after the last die, the Nitinol/silver cable had a diameter of approximately 0.0085"±0.0005". The so-formed Nitinol/silver cable was then annealed for approximately one minute at a temperature of approximately 500° C. to remove the effects of cold-working from the cable. Pieces of the resulting twisted and drawn Nitinol/silver cable were then subjected to bend radius testing by wrapping pieces of the cables around pins of different diameters and by clamping the cable back on itself with a pair of pliers to simulate a zero-diameter bend. Comparison tests were conducted on 0.008" diameter Nitinol wires (single strand). The results of the bend radius testing are set forth in Table 2, with percent recovery calculated according to $(180°-x°)/180°$, where $x°$ is the angle of set taken by the wire or cable from longitudinal axis of the wire after the bend:

TABLE 2

| Pin Diameter (inch) | % Recovery NiTi/Ag cable | % Recovery NiTi Wire |
|---|---|---|
| .247 | 100 | 99.17 |
| .231 | 99.94 | 99.17 |
| .201 | 99.94 | 99.44 |
| .169 | 99.89 | 99.44 |
| .139 | 98.61 | 99.56 |
| .109 | 98.56 | 98.33 |
| .078 | 99.50 | 98.22 |
| .050 | 97.22 | 92.50 |
| .036 | 96.67 | 70.00 |
| .024 | 95.00 | 56.67 |
| 0 diameter bend | 55.56 | 47.22 |

From the results of the tests set forth in Table 2, it will be appreciated that the Nitinol/silver cable of the invention exhibited substantially the same flexibility relative to the same diameter Nitinol wire, except in the range of a bend diameter of 0.050" to 0.024" and smaller where the NiTi/Ag cable exhibited enhanced flexibility. Thus, the recoverable elastic strain of the Nitinol/silver cable was equal to or higher than the recoverable elastic strain of the Nitinol wire. Furthermore, it is believed that the Nitinol/silver cable of the invention exhibited high elastic characteristics without the Nitinol entering the stress-induced martensite phase. In addition to the increased flexibility, the Nitinol/silver cable of the invention exhibited increased radiopacity relative to the same diameter Nitinol wire.

EXAMPLE 3

Illustrated by FIGS. 4 and 5 described above, four strands of 0.005 inch diameter Nitinol wire were helically twisted about a single strand of 0.003 inch diameter platinum-iridium (88-12) core wire at a lay length of approximately 0.050 inches to form a wire rope of approximately 0.013" diameter. The rope was fed through successive dies of approximately 0.012", 0.0105", 0.009", and 0.0075" diameters to form a NiTi/PtIr cable. After each die, the cable rebounded to a slightly larger diameter than the diameter of the die. Thus, after the last die, the NiTi/PtIr cable had a diameter of 0.0085"±0.0005". The so-formed NiTi/PtIr cable was then annealed for approximately one minute at a temperature of approximately 500° C. to remove the effects of cold-working from the cable. Pieces of the resulting twisted and drawn NiTi/PtIr cable were then subjected to bend radius testing by wrapping pieces of the cables around pins of different diameters and by clamping the cable back on itself with a pair of pliers to simulate a zero-diameter bend. Comparison tests were conducted on 0.008" diameter Nitinol wires (single strand). The results of the bend radius testing are set forth in Table 3, with percent recovery calculated according to $(180°-x°)/180°$, where $x°$ is the angle of set taken by the wire or cable from longitudinal axis of the wire after the bend:

TABLE 3

| Pin Diameter (in) | % Recovery NiTi/Pt-Ir cable | % Recovery NiTi Wire |
|---|---|---|
| .247 | 98.33 | 99.17 |
| .231 | 98.89 | 99.17 |
| .201 | 98.89 | 99.44 |
| .169 | 97.78 | 99.44 |
| .139 | 97.22 | 99.56 |
| .109 | 95.56 | 98.33 |
| .078 | 96.11 | 98.22 |
| .050 | 96.67 | 92.50 |
| .036 | 95.83 | 70.00 |
| .024 | 95.00 | 56.67 |
| 0 diameter bend | 88.89 | 47.22 |

From the results of the tests set forth in Table 3, it will be appreciated that the NiTi/PtIr cable of the invention exhibited substantially the same flexibility relative to the same diameter Nitinol wire, except in the range of a bend diameter of 0.036" to 0.024" and smaller where the NiTi/PtIr cable exhibited enhanced flexibility. Thus, the recoverable elastic strain of the Nitinol/platinum-iridium cable was substantially equal to or higher than the recoverable elastic strain of the Nitinol wire. Furthermore, it is believed that the NiTi/PtIr cable of the invention exhibited high elastic characteristics without the Nitinol entering the stress-induced martensite phase. In addition to the increased flexibility, the NiTi/PtIr cable of the invention exhibited increased radiopacity relative to the same diameter Nitinol wire.

EXAMPLE 4

Six strands of 0.006 inch diameter Nitinol wire are helically twisted about a single strand of 0.006 inch diameter silver core wire at a lay length of approximately 0.080 inches to form a wire rope of approximately 0.018" diameter, and fed through successive dies of 0.017", 0.015", 0.014", 0.013", and 0.012" diameters to form a NiTi/Au cable. After each die, the NiTi/Au cable rebounds to a slightly larger diameter than the diameter of the die. Thus, after the last die, the cable has a diameter of approximately 0.013" rather than 0.012". The so-formed NiTi/Au cable is then annealed for approximately one minute at a temperature of approximately 500° C. to remove the effects of cold-working from the cable. The resulting cable exhibits favorable flexibility and radiopacity characteristics. The cable may be used as stent wire or wire for a guidewire. If desired, a portion of the NiTi/Au cable may be ground down to a smaller diameter, and the smaller diameter portion will exhibit favorable flexibility and radiopacity characteristics.

EXAMPLE 5

Three strands of 0.010 inch diameter 51–49 nickel-titanium alloy wire are helically twisted about a single strand of 0.004 inch diameter gold core wire at a lay length of approximately 0.080 inches to form a wire rope of approximately 0.022" diameter. The wire rope is fed through successive dies of 0.020", 0.018", 0.016", 0.014", and 0.012" diameters to form a NiTi/Au cable. After each die, the NiTi/Au cable rebounds to a slightly larger diameter than the diameter of the die. Thus, after the last die, the NiTi/Au cable has a diameter of approximately 0.013" rather than 0.012". The so-formed cable is then annealed for approximately one minute at a temperature of approximately 500° C. to remove the effects of cold-working from the cable. The resulting cable exhibits extremely favorable flexibility and radiopacity characteristics.

EXAMPLE 6

Figure 6:
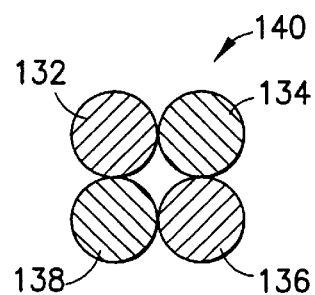
FIG. 6 is a cross sectional view another exemplar wire rope prior to being drawn through a die according to the invention.
Figure 7:
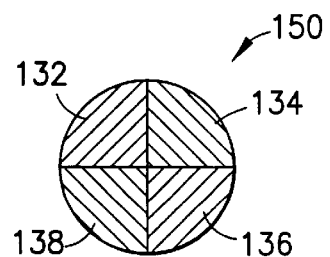
FIG. 7 is a cross sectional view of a cable formed from the wire rope in FIG. 6.

As seen in FIGS. 6 and 7 which represent a less preferred embodiment of the invention, three strands 132, 134, 136 of 0.008 inch diameter nickel-titanium alloy (50%—50%) wire and one strand 138 of 0.008 inch diameter silver wire are helically twisted about each other at a lay length of approximately 0.080 inches to form a wire rope 140 of approximately 0.016" diameter. The rope is fed through successive dies of 0.014", 0.012", 0.010", and 0.009" diameters to form a NiTi/Ag cable 150. After each die, the NiTi/Ag cable 150 rebounds to a slightly larger diameter than the diameter of the die. Thus, after the last die, the cable has a diameter of approximately 0.010" rather than 0.009". The so-formed cable 150 is then annealed for approximately one minute at a temperature of approximately 500° C. to remove the effects of cold-working from the cable. The resulting cable 150 exhibits extremely favorable flexibility and radiopacity characteristics.

There have been described and illustrated herein several embodiments of cables which exhibit favorable flexibility and radiopacity characteristics. While particular embodiments of the invention have been described, it is not intended that the invention be limited thereto, as it is intended that the invention be as broad in scope as the art will allow and that the specification be read likewise. Thus, while particular numbers of strands with particular diameters have been disclosed, it will be appreciated that different numbers of strands (e.g., two around one, five around one, six or more around one, three around none, five around none, six or more around none, etc.) and different diameters could be utilized. In fact, the outer wires need not be the same size as each other, nor the same size as the core wire where a core wire is used. In addition, while the core wire, where present, has been disclosed as a single high density strand formed from silver, gold or platinum-iridium, it will be appreciated that core wire could be made from other high density materials, from a combination of high density materials (e.g., Au and Ag), or may constituted from a high density cable made from one or more materials. Similarly, while a radioactive core wire was disclosed, it will be appreciated that the radioactive wire need not be used as a core wire but could be present as one of the wires of a non-core wire embodiment. Also, while the strands have been shown with a helical twist and with particular lay lengths, it will be recognized that other types of twining of strands could be used and other lay lengths could be utilized with similar results obtained. Indeed, as the lay length is decreased, the resulting cable will be more flexible. Moreover, while particular configurations have been disclosed in reference to the number of dies used and the specific reduction in diameter of the rope, it will be appreciated that other configurations could be used as well provided the reduction in diameter is at least 20%, and preferably at least 30%. Further, while annealing at a certain temperature for a particular length of time was described, it will be appreciated that other temperatures, times, and methods could be utilized to substantially eliminate the cold working in the cable to achieve optimal superelastic properties. It will therefore be appreciated by those skilled in the art that yet other modifications could be made to the provided invention without deviating from its spirit and scope as so claimed.

What is claimed is:

1. A radiopaque cable, comprising:
   at least two nickel-titanium wires twined about a core wire and drawn through at least one die to form a flexible cable having a substantially circular cross section, wherein said core wire comprises at least one of gold, silver, and platinum-iridium, and has a density substantially greater than the density of said nickel-titanium wires.

2. A radiopaque cable according to claim 1, wherein:
   said at least two twined nickel-titanium wires comprises at least three nickel-titanium wires twisted about said core wire.

3. A radiopaque cable according to claim 2, wherein:
   the cross sectional diameter of said flexible cable is approximately 20–50% smaller than the overall cross sectional diameter of said at least three twisted nickel-titanium wires twined around said core wire.

4. A radiopaque cable according to claim 1, wherein:
   said at least one die comprises a plurality of dies of increasingly smaller openings.

5. A radiopaque cable according to claim 1, wherein:
   said core wire is radioactive.

6. A radiopaque cable according to claim 1, wherein:
each of said twined wires and said core wire have the same diameter.

7. A radiopaque cable according to claim 1, wherein:
said core wire has a first diameter, and at least one of said twined wires has a second diameter different from said first diameter.

8. A radiopaque cable according to claim 1, wherein:
said core wire is a flexible core cable having a substantially circular cross section.

9. A radiopaque cable according to claim 1, wherein:
said flexible cable has a substantially uniform first diameter, and said flexible cable has an end portion which is ground to a second diameter which is smaller than said first diameter.

10. A radiopaque cable, comprising:
at least two nickel-titanium wires and a relatively higher density wire comprised of at least one of gold, silver, and platinum-iridium and having a density substantially greater than the density of said nickel-titanium wires, said at least two nickel-titanium wires and said relatively higher density wire being twined and drawn through at least one die to form a flexible cable having a substantially circular cross section.

11. A radiopaque cable according to claim 10, wherein:
said at least two twined nickel-titanium wires comprises at least three nickel-titanium wires.

12. A radiopaque cable according to claim 11, wherein:
the cross sectional diameter of said flexible cable is approximately 20–50% smaller than the overall cross sectional diameter of said at least three twisted nickel-titanium wires and said relatively higher density wire.

13. A radiopaque cable according to claim 10, wherein:
said relatively higher density wire has a first diameter, and at least one of said nickel-titanium wires has a second diameter different from said first diameter.

14. A radiopaque cable according to claim 10, wherein:
said relatively higher density wire is radioactive.

15. A method of making a flexible radiopaque cable, comprising:
a) twisting at least two strands of nickel-titanium wire about a core wire comprised of at least one of gold, silver, and platinum-iridium and having a higher density than said nickel-titanium to form a wire rope; and b) drawing the wire rope through at least one die to form a cable having a substantially circular cross section.

16. A method according to claim 15, wherein:
said drawing step comprises successively drawing said wire rope through a plurality of dies of decreasing diameter to reduce the overall cross sectional diameter of said wire rope by approximately 20–50%.

17. A method according to claim 15, wherein:
said core wire having a higher density than said nickel-titanium is formed from at least one of gold, silver, and platinum-iridium.

18. A method according to claim 15, wherein:
said at least two strands comprises at least three strands.

19. A method according to claim 18, further comprising:
c) annealing the cable to remove the effects of cold-working.

20. A method of making a flexible radiopaque cable, comprising:
a) twisting at least two strands of nickel-titanium wire about a core wire having a higher density than said nickel-titanium to form a wire rope;
b) drawing the wire rose through at least one die to form a cable having a substantially circular cross section;
c) annealing the cable to remove the effects of cold-working; and
d) cutting said cable to a desired length, and grinding an end portion of said length to a smaller diameter than the remainder of said length.

21. A method of making a flexible radiopaque cable, comprising:
a) twisting at least two strands of nickel-titanium wire and an additional wire comprising at least one of gold, silver and platinum-iridium and having a higher density than said nickel-titanium to form a wire rope; and
b) drawing the wire rope through at least one die to form a cable having a substantially circular cross section.

22. A method according to claim 20, wherein:
said at least two strands comprises at least three strands.

23. A method according to claim 20, wherein:
said drawing step comprises successively drawing said wire rope through a plurality of dies of decreasing diameter to reduce the overall cross sectional diameter of said wire rope by approximately 20–50%.

* * * * *